United States Patent
DiGasbarro

(10) Patent No.: US 8,245,857 B2
(45) Date of Patent: Aug. 21, 2012

(54) MEDICAL DEVICE HOLDER ASSEMBLY

(75) Inventor: Phillip Peter DiGasbarro, St. Louis, MO (US)

(73) Assignee: Trademark Medical, LLC, St. Louis, MO (US)

( * ) Notice: Subject to any disclaimer, the term of this patent is extended or adjusted under 35 U.S.C. 154(b) by 418 days.

(21) Appl. No.: 12/457,574

(22) Filed: Jun. 16, 2009

(65) Prior Publication Data

US 2009/0308823 A1    Dec. 17, 2009

Related U.S. Application Data

(60) Provisional application No. 61/061,724, filed on Jun. 16, 2008.

(51) Int. Cl.
*A47F 7/00* (2006.01)
(52) U.S. Cl. .................................................. 211/85.13
(58) Field of Classification Search ............... 211/85.13, 211/13.1, 60.1, 71.01, 113, 119; 206/438, 206/363; D24/128; 47/41.12; 15/160; 433/177, 433/77; 604/246, 192
See application file for complete search history.

(56) References Cited

U.S. PATENT DOCUMENTS

| | | | |
|---|---|---|---|
| 1,096,180 A | 5/1914 | Meurling | |
| 2,191,782 A * | 2/1940 | Valane | 248/229.26 |
| 2,767,704 A * | 10/1956 | Bailey | 600/549 |
| 2,943,745 A * | 7/1960 | Bjornson | 211/60.1 |
| 3,967,766 A * | 7/1976 | Hart | 223/85 |
| 3,987,807 A * | 10/1976 | Varnell | 135/66 |
| 4,336,806 A | 6/1982 | Eldridge, Jr. | |
| 4,418,496 A | 12/1983 | Koistinen | |
| 4,447,238 A | 5/1984 | Eldridge, Jr. | |
| 4,597,551 A | 7/1986 | Ciechanowski et al. | |
| 4,823,444 A * | 4/1989 | Larsen | 24/716 |
| 5,033,737 A * | 7/1991 | Moye | 482/17 |
| 5,224,679 A | 7/1993 | Code | |
| 5,279,578 A * | 1/1994 | Cooke | 604/192 |
| 5,385,468 A * | 1/1995 | Verderber | 433/28 |
| 5,411,193 A * | 5/1995 | Culp | 224/669 |
| 5,429,615 A * | 7/1995 | Starchevich | 604/246 |
| 5,498,242 A * | 3/1996 | Cooke | 604/192 |
| 5,752,286 A | 5/1998 | Wright | |
| 5,806,822 A * | 9/1998 | Schulz | 248/309.1 |
| 5,871,189 A | 2/1999 | Hoftman | |
| 5,915,963 A | 6/1999 | Homra | |
| 5,927,974 A | 7/1999 | Homra | |
| 6,077,074 A | 6/2000 | Homra | |
| 6,176,378 B1 * | 1/2001 | Neubauer et al. | 211/113 |
| 6,367,110 B1 | 4/2002 | Urueta et al. | |
| 6,645,185 B2 | 11/2003 | Bird et al. | |
| D541,933 S | 5/2007 | White et al. | |
| 7,320,681 B2 | 1/2008 | Gillis et al. | |

(Continued)

*Primary Examiner* — Sarah Purol
(74) *Attorney, Agent, or Firm* — Diederiks & Whitelaw, PLC

(57) ABSTRACT

A medical device holder assembly includes a medical storage device for storing a medical instrument on a support rail convenient to a patient. The storage device includes a housing and a universal attachment member which forms an elastomeric loop adapted to secure the housing to the support rail. The storage device includes a locking slot formed in an upper portion adapted to receive at least a portion of the instrument to retain the instrument within the housing. The housing may also include an internal retention mechanism to aid in retaining the device within the housing, as well as air holes, drain holes, external hooks for retaining the elastomeric loop in place, external retention features to aid in retaining the storage device in place on the support rail, and/or a sump to prevent the instrument from contacting fluid in the bottom of the housing.

22 Claims, 7 Drawing Sheets

U.S. PATENT DOCUMENTS

| | | |
|---|---|---|
| 7,431,255 B2 * | 10/2008 | Pulido .................. 248/309.1 |
| 2004/0035743 A1 * | 2/2004 | Tighe et al. ............. 206/571 |
| 2005/0194507 A1 * | 9/2005 | White .................... 248/314 |
| 2005/0230280 A1 | 10/2005 | Sotiropolous et al. |
| 2006/0192064 A1 | 8/2006 | White et al. |
| 2006/0229567 A1 | 10/2006 | Wright |
| 2006/0278781 A1 | 12/2006 | Homra et al. |
| 2007/0057129 A1 | 3/2007 | White et al. |
| 2007/0199846 A1 | 8/2007 | Wright |
| 2007/0210018 A1 * | 9/2007 | Wallwiener et al. ......... 211/13.1 |
| 2009/0166306 A1 * | 7/2009 | Ahearn .................. 211/85.13 |
| 2011/0177470 A1 * | 7/2011 | Jones ..................... 433/77 |

* cited by examiner

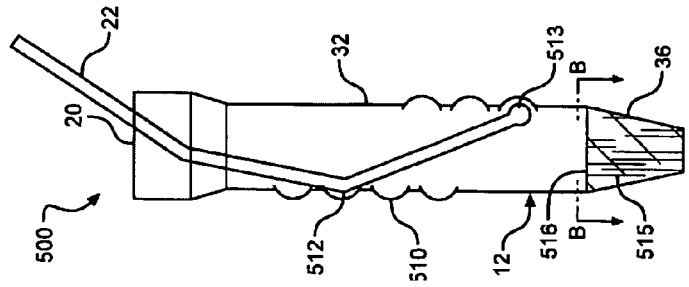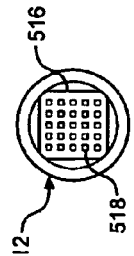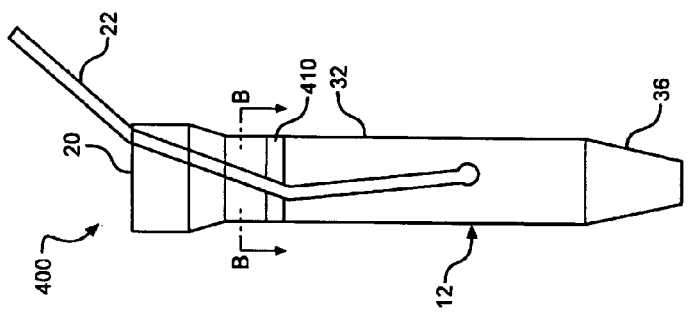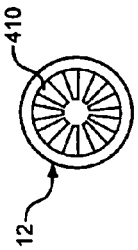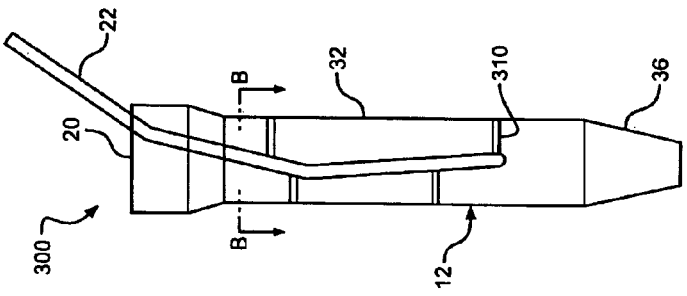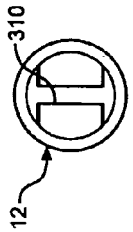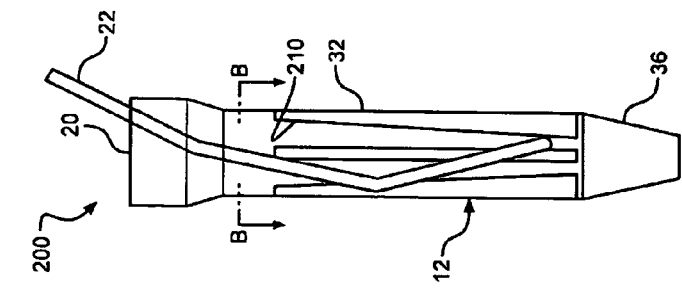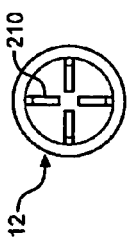

MEDICAL DEVICE HOLDER ASSEMBLY

CROSS-REFERENCE TO RELATED APPLICATIONS

The present invention claims the benefit of U.S. Provisional Patent Application Ser. No. 61/061,724 entitled "Medical Device Holder" filed Jun. 16, 2008.

BACKGROUND OF THE INVENTION

1. Field of the Invention

The present invention pertains to the art of medical device holders and, more particularly, to medical device holders that may be utilized at a variety of locations.

2. Discussion of the Prior Art

Medical instruments, such as trocars, scalpels, thermometers and yankauer suction devices, are used to treat patients in healthcare facilities and in the home. Some devices are intended to be used repeatedly on a single patient, and may be used for up to 24 hours or more. The replacement of these medical instruments is based on functional and infection control considerations that may be unique for each instrument. Among the considerations used to determine the replacement frequency of these instruments is the control of accidental contamination from contact with environmental surfaces. It is well known that exposure to microbes found on environmental surfaces, such as table tops, intravenous (IV) poles, bed linens and floors, could adversely affect the health of the patient. Likewise, healthcare workers, care providers and family members can be exposed to potentially harmful microbes found in secretions and fluids from the patient. Contamination of environmental surfaces from used medical devices can also lead to contamination of subsequent patients if microbes are not removed or killed during the cleaning process. Therefore, it is useful to have a means to store these medical instruments to protect both the patient and others from harm caused by exposure to microbes.

Additionally, it is important to assure that the medical instrument is available for use when needed during treatment of the patient. In some cases, it is desirable to be able to temporarily store medical instruments in a storage device during patient transport between different parts of a medical facility, during ambulance transport or in other circumstances where patient care instruments must be used to treat the patient.

In the absence of appropriate holders, users have been known to store medical instruments in open graduated cylinders, under bed pillows, by hanging over IV poles or back in the original packaging. These methods encourage accidental contact with potentially contaminated surfaces, as well as allowing the accumulation of secretions from previous uses. In an attempt to address this problem, various storage devices have been developed to store and protect medical instruments, including those disclosed in U.S. Pat. Nos. 5,915,963; 5,927,974 and 6,077,074 to Homra, U.S. Pat. No. 4,597,551 to Ciechanowski et al.; U.S. Pat. No. 5,752,286 to Wright; U.S. Patent Application Publication No. 2006/0192064 to White et al.; and U.S. Design Pat. No. D541,933 to White et al.

In some cases, the mechanisms used to attach such storage devices to bed rails, IV poles, head boards and other equipment are elaborate and expensive. By design and cost, these attachment mechanisms are often intended to be used with multiple storage devices during the course of treatment for one patient, and are very often used for the treatment of multiple patients. Repeated use of the attachment mechanisms, and reusable attachment mechanisms in particular, can create infection control risks if decontamination is incomplete, and in some cases complete decontamination may not be possible at all.

In addition, bed rails, IV poles, head boards and other equipment often have dimensions of differing sizes and geometries that make the use of a single attachment mechanism very expensive or even unachievable. For example, while an IV pole is generally cylindrical and uniform with a circular cross-section, a bed rail may be oval or rectangular in cross-section.

Some of the patent documents noted above disclose multiple attachment mechanisms to accommodate different sizes and types of rails, poles and equipment. However, a single, universal mechanism that accommodates these varying geometries while allowing for stable, secure attachment at a preferred, convenient location near the point of patient care, and that can be effectively decontaminated for infection control purposes, has not been developed and is not disclosed in the storage devices referenced above. In addition, the prior art fails to address the need to securely retain the medical instrument within the holder until needed. Therefore, there is seen to exist a need for a storage device that can be positioned where needed, that can effectively retain a medical instrument in a storage position and that allows for effective infection control practices.

SUMMARY OF THE INVENTION

The present invention is directed to a medical device holder and method for safely storing a medical device. The medical device holder can be attached to a plurality of different support structures to retain a medical device at a convenient location near a patient. The medical device holder includes an elongated housing which defines a storage area for a medical device, such as a yankauer suction device. A slot in the housing is sized such that a portion of the medical device to be retained by the medical device holder can be inserted into the slot to secure the medical device to the housing. An elastomeric band is threaded through apertures in the housing, wrapped around a desired support structure, and secured in place with a fastener to retain the housing in place against the support structure. Alternatively, the elastomeric band can be wrapped around both the housing and the support structure, and secured in place with the fastener to retain the housing against the support structure. Optionally, the housing can include outer structure which aids in retention of the medical device holder against the support structure, as well as internal structure which aides in retention of a medical device within the holder. Additional features such as airflow holes, internal instrument retention structures, a sump, drain holes, and external fastener retention structures may also be incorporated into the medical device holder.

Additional objects, features and advantages of the present invention will become more readily apparent from the following detailed description of preferred embodiments when taken in conjunction with the drawings wherein like reference numerals refer to corresponding parts in the several views.

BRIEF DESCRIPTION OF THE DRAWINGS

FIG. 8A is a cross-sectional side view of an alternative storage device including a first internal retention mechanism;

FIG. 8B is a cross-sectional top view of the storage device of FIG. 8A;

FIG. 9A is a cross-sectional side view of an alternative storage device including a second internal retention mechanism;

FIG. 9B is a cross-sectional top view of the storage device of FIG. 9A;

FIG. 10A is a cross-sectional side view of an alternative storage device including a third internal retention mechanism;

FIG. 10B is a cross-sectional top view of the storage device of FIG. 10A;

FIG. 11A is a cross-sectional side view of an alternative storage device including a fourth internal retention mechanism and a sump;

FIG. 11B is a cross-section top view of the storage device of FIG. 11A;

DETAILED DESCRIPTION OF THE PREFERRED EMBODIMENTS

Figure 1:
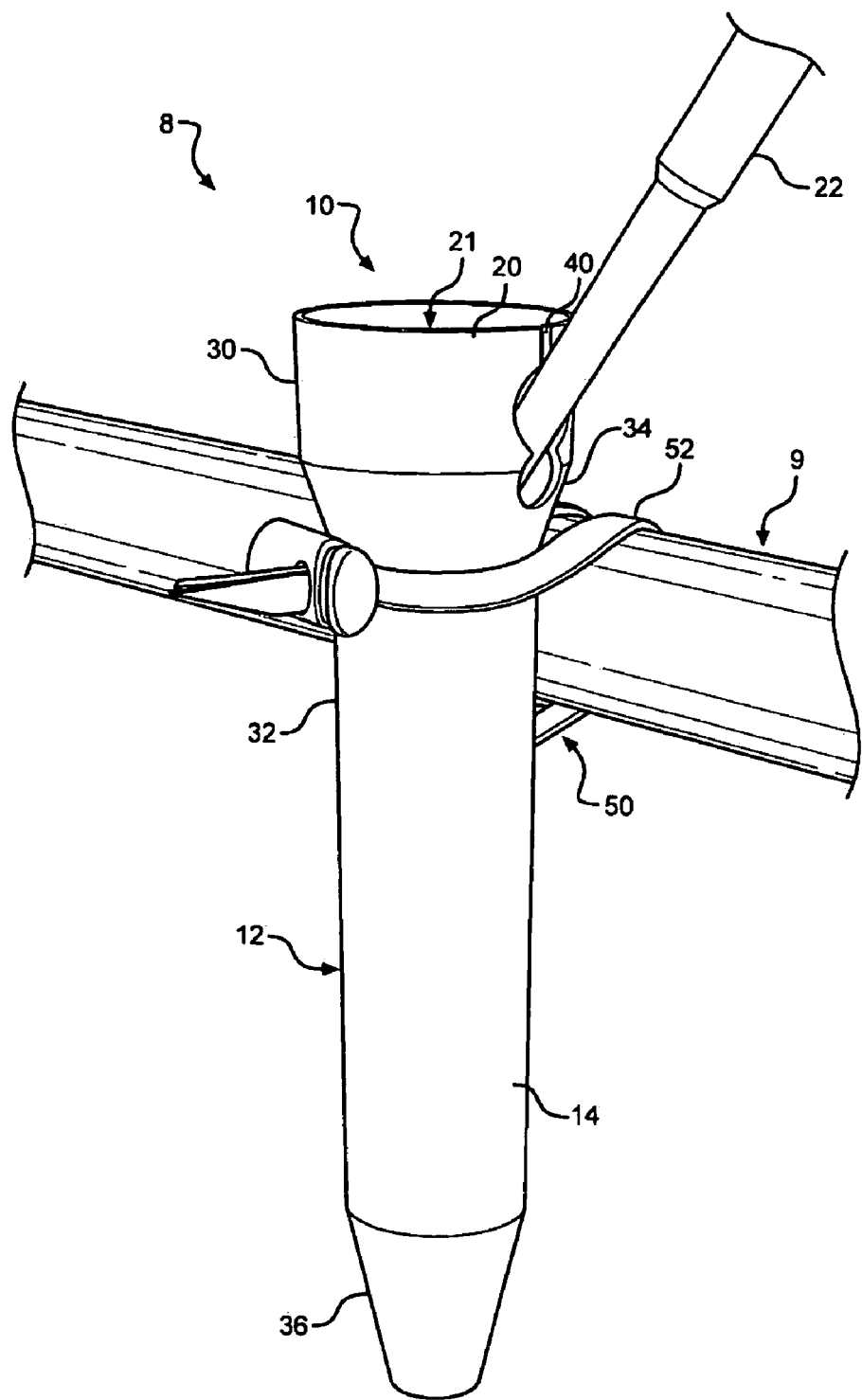
FIG. 1 is a perspective view of a medical instrument storage assembly of the present invention including a storage device storing a yankauer suction device.

With initial reference to FIG. 1, a medical instrument holder assembly 8 is shown including a support surface, such as a rail 9, and a storage device 10 of the present invention mounted thereto. Storage device 10 includes a main body 12 having at least one sidewall 14 defining an elongated instrument housing 20 having an opening 21 through which a medical instrument 22 may be inserted. Preferably, instrument housing 20 is constructed of a semi-rigid plastic. However, housing 20 may alternatively be constructed from fully rigid or flexible materials, or a combination thereof. In a preferred embodiment, main body 12 includes an upper portion 30 that tapers to a middle portion 32. Preferably, upper portion 30 and middle portion 32 both include generally cylindrical diameters, wherein the diameter of upper portion 30 is larger than the diameter of middle portion 32, forming a shelf portion 34 there between. Middle portion 32, in turn transitions to a tapered bottom portion 36. Extending through upper portion 30 is a locking slot 40 which may be utilized to secure medical instruments 22 within storage device 10 as will be discussed in more detail below. Additionally, main body 12 preferably includes an attachment means for connecting universal attachment mechanism 50 to main body 12. This attachment means can be in the form of a large staple or the like (not shown) attached to an outer portion of main body 12, which can be utilized to loosely affix universal attachment mechanism 50 to main body 12. In a preferred embodiment of the invention depicted in FIG. 2, the attachment means is in the form of first and second apertures 42 and 43 extending through middle portion 32 of main body 12, which may be utilized to retain a universal attachment mechanism 50 as will be discussed in more detail below.

Figure 2:
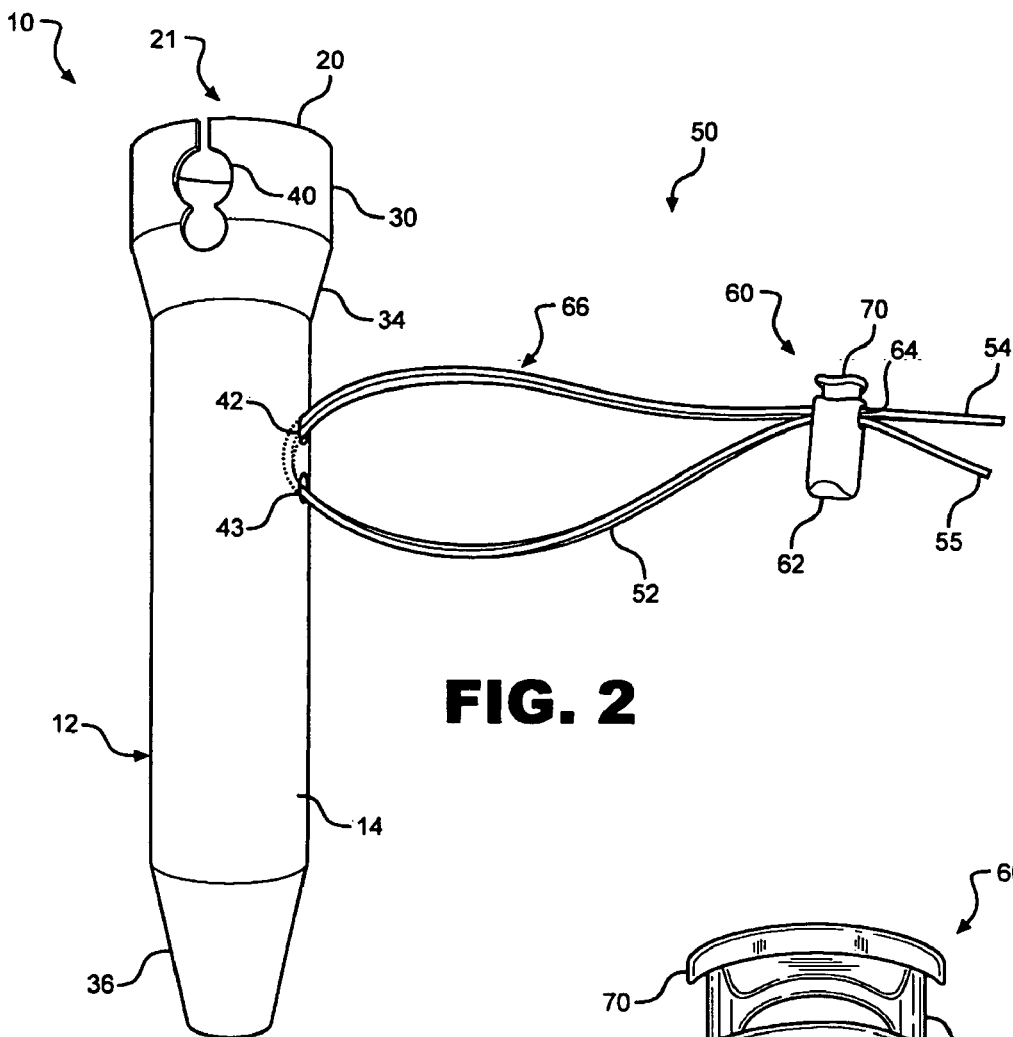
FIG. 2 is a perspective view of the storage device of FIG. 1.
Figure 3:
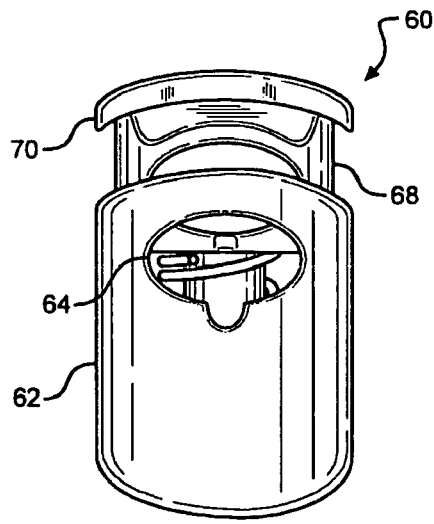
FIG. 3 is an enlarged view of the universal attachment devise of FIGS. 1 and 2 in a partially compressed position.

As depicted in FIGS. 1 and 2, universal attachment mechanism 50 is in the form of an elastomeric band member 52 having first and second ends 54 and 55. Elastomeric band member 52 can be threaded through apertures 42 and 43 to aid in retention of storage device 10 against support rail 9 as will be described in more detail below. As best seen in FIGS. 2 and 3, universal attachment mechanism 50 includes a fastener 60 having a housing 62 including at least one aperture 64 through which first and second ends 54 and 55 of elastomeric band member 52 can be threaded to form an elastomeric loop 66. A retention mechanism 68 is adapted to selectively secure elastomeric band member 52 against housing 20. In a preferred embodiment, retention mechanism 68 is in the form of a spring-biased retention mechanism or clamp 68 including a user interface portion 70 adapted to selectively clamp elastomeric band member 52 against housing 62 of fastener 60 and lock elastomeric member 52 to fastener 60. In accordance with the invention, storage device 10 is adapted to be secured to support surface 9, such as a bed rail, IV pole, head board, a headwall, and other equipment by attachment mechanism 50, which exerts a force that urges storage device 10 against the bed rail, IV pole, head board rail or other equipment.

Figure 4:
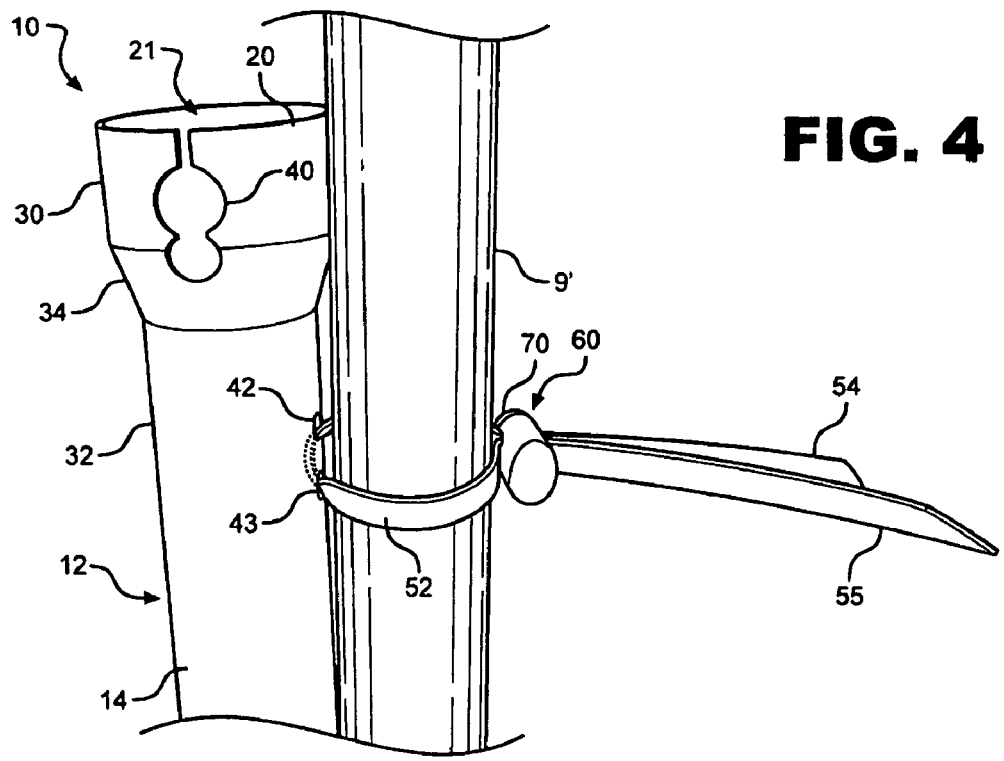
FIG. 4 is a partial view of the storage device of FIG. 1 attached to a vertical support rail by a first attachment method.

FIG. 4 depicts storage device 10 attached to a vertical support rail 9' via attachment mechanism 50 in a first attachment configuration. Preferably, storage device 10 will be shipped to a user in the configuration shown in FIG. 2. That is, universal attachment mechanism 50 will be attached to housing 20 through apertures 42 and 43. However, the universal attachment mechanism 50 may alternatively be shipped detached from housing 20. Regardless, when medical storage device 10 is in the configuration shown in FIG. 2, a user may easily remove fastener 60 from the elastomeric band member 52, wrap the first and second ends 54 and 55 of elastomeric band member 53 around opposing sides of support rail 9', insert first and second ends 54 and 55 back through the aperture 64 in fastener 60 to form elastomeric loop 66, and slide fastener 60 distally and proximally along first and second ends 54 and 55 of elastomeric band member 53 to adjust elastomeric loop 66 around support rail 9' to secure medical storage device 10 to support rail 9'.

When elastomeric band member 52 is shipped detached from main body 12, elastomeric band member 52 can be attached to main body 12 by first removing fastener 60 from the elastomeric band member 52. Next, one of the first and second ends 54 and 55 of elastomeric band member 52 is fed through one of apertures 42 and 43 into housing 20, and then fed out of housing 20 through the other of apertures 42 and 43 such that elastomeric band member 52 is looped through housing 20. A user then depresses user interface portion 70 of clamp 60 and feeds the first and second ends 54 and 55 of elastomeric band member 52 through the at least one aperture 64 in fastener 60. The user then releases user interface portion 70, thereby clamping elastomeric band member 52 to fastener 60 and creating an elastomeric loop 66.

Figure 5:
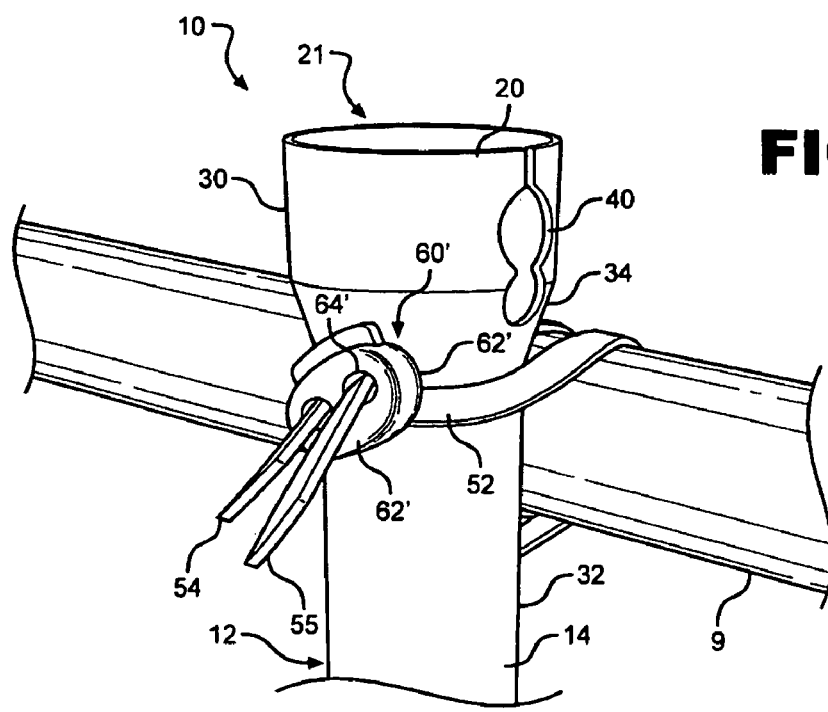
FIG. 5 is a partial view of the storage device of FIG. 1, including an alternative fastener, attached to a horizontal support rail by a second attachment method.

One of the advantages of the present invention is the ability of a user to attach storage device 10 to a support surface in a number of different configurations. FIG. 5 depicts an alternative attachment method whereby storage device 10 is attached to a horizontal bed rail 9. With this method, storage device 10 is held against a bed rail 9, and elastomeric loop 66 is stretched underneath bed rail 9, over bed rail 9, and looped over upper portion 30 of main body 12. Alternatively, elastomeric loop 66 may be stretched over the top of bed rail 9, and looped over tapered bottom portion 36 of main body 12. It should be understood that elastomeric loop 66 provides a biasing force to hold main body 12 against bed rail 9. Note that an alternative fastener 60' is depicted including a housing 62' having two adjacent apertures 64' through which first and second ends 54 and 55 of elastomeric band member 52 can be threaded, respectively, to form an elastomeric loop 66. Although not depicted, it should be understood that the same attachment method could be utilized to attach storage device 10 to a vertical rail, such as 9' shown in FIG. 4. More specifically, elastomeric loop 66 may be stretched around bed rail 9' and looped over upper portion 30 of main body 12, or alternatively, stretched around bed rail 9' and looped over tapered bottom portion 36 of main body 12.

At this point, a user may reposition fastener 60' to close elastomeric loop 66 tighter around main body 12. However, elastomeric band member 52 is preferably sized such that an elastomeric loop 66 created by attaching fastener 60' to elastomeric band member 52 can be stretched to fit over a standard bed rail and upper portion 30 of main body 12 such that, when a user releases elastomeric loop 66, the elastic nature of the material will bias elastomeric loop 66 against main body 12 to retain medical storage device 10 in place against bed rail 9. The adjustable nature of elastomeric loop 66 is important to assure that the storage device 10 is held firmly in place to prevent sliding on, or rotation around bed rail 9, particularly if bed rail 9 is in a non-horizontal position. Note that, when positioned against bed rail 9, upper portion 30 of main body 12 provides a means for supporting storage device 10 on bed rail 9. That is, shelf portion 34 rests against a top portion of bed rail 9, which prevents upper portion 30 from sliding past bed rail 9 and aids in supporting medical storage device 10 against bed rail 9. In addition, upper portion 30 prevents elastomeric loop 66 from slipping over the top of storage device 10 after being secured to bed rail 9 or vertical support rail 9'.

Figure 6:
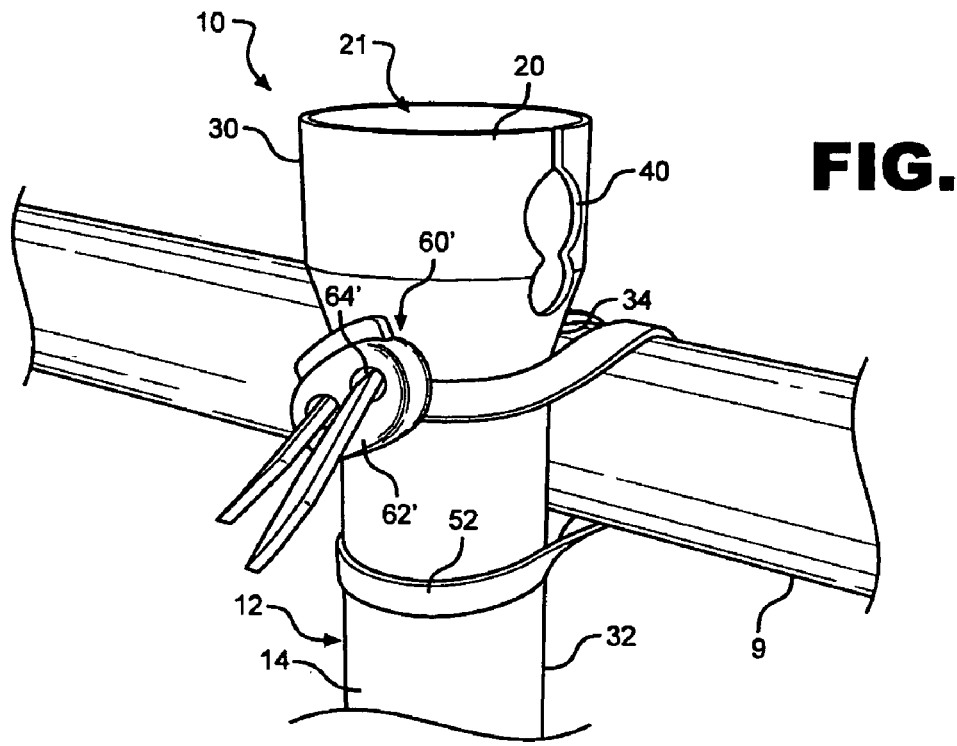
FIG. 6 is a partial view of the storage device of FIG. 1 attached to a horizontal support rail by a third attachment method.

In an alternative arrangement depicted in FIG. 6, attachment mechanism 50 is not directly attached to storage device 10, but instead is held in place against bed rail 9 by looping elastomeric loop 66 around bed rail 9 and storage device 10. More specifically, first and second ends 54 and 55 of elastomeric band member 52 are first fed through respective apertures 64' of fastener 60' and clamped in place to form elastomeric loop 66. Next, elastomeric loop 66 is looped around middle portion 32 of main body 12, stretched under bed rail 9, and stretched to extend over the top of bed rail 9 and loop over upper portion 30 of main body 12. If necessary, elastomeric loop 66 may be tightened by additional looping or twisting of elastomeric band member 52 or, more preferably, by adjusting the position of fastener 60' on elastomeric loop 66. Alternatively, elastomeric loop 66 may be looped around middle portion 32 of main body 12, stretched over the top of bed rail 9, and looped over tapered bottom portion 36 of main body 12.

Figure 7:
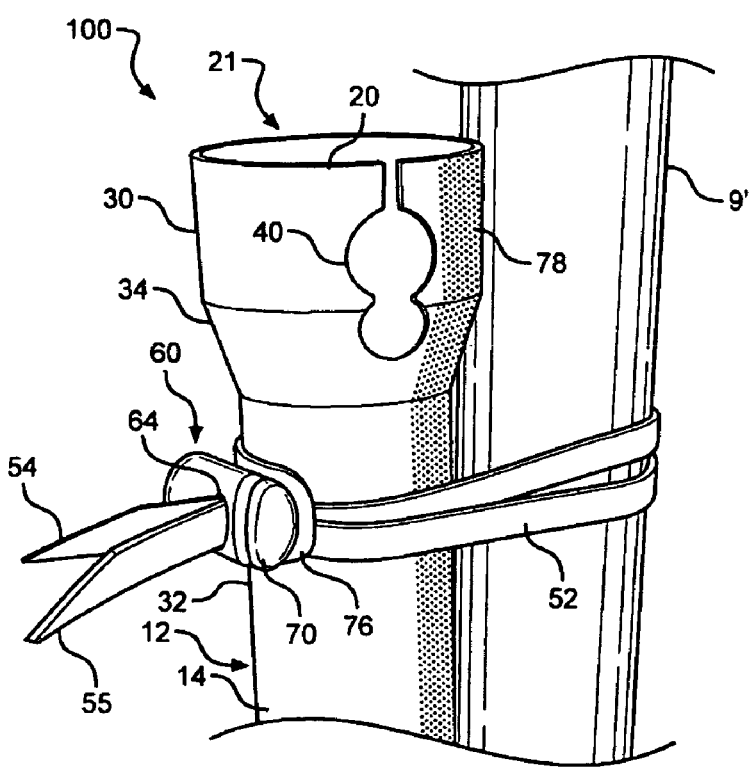
FIG. 7 is a partial view of the storage device of FIG. 1 attached to a vertical support rail by a fourth attachment method.

An alternative attachment method is depicted in FIG. 7, wherein an alternative storage device 100 is secured to a vertical support rail 9'. In this alternative arrangement, fastener 60 and elastomeric band member 52 are used like a toggle and loop to secure storage device 100 to IV pole 9'. More specifically, first and second ends 54 and 55 of elastomeric band member 52 are fed through aperture 64 of fastener 60 and clamped in place to form elastomeric loop 66. Next, while holding storage device 100 in place against IV pole 9', a user holds fastener 60 against storage device 100 and stretches an end 76 of elastomeric loop 66 around middle portion 32 of housing 20, around IV pole 9', and then loops end 76 of elastomeric loop 66 around fastener 60. The elastic nature of band member 52 acts to hold storage device 100 against IV pole 9', while upper portion 30 of housing 20 prevents storage device 100 from sliding down pole 9' past attachment mechanism 50. As depicted in FIG. 7, alternative storage device 100 additionally includes an external retention feature in the form of molded-in surface texture 78 which provides a high-friction surface that aids in the retention of storage device 100 against pole 9'.

In addition to locking slot 40, the storage device of the present invention may include various internal retention mechanisms as depicted in FIGS. 8A-11B. More specifically, FIG. 8A depicts a storage device 200 in accordance with the present invention including longitudinally tapered ribs 210 which extend along the length of middle portion 32. In a preferred embodiment, four tapered ribs 210 are equally spaced within instrument housing 20 as depicted in FIG. 8B. Tapered ribs 210 provide a frictional force to hold a medical instrument in place within instrument housing 20. FIGS. 9A and 9B depict an alternative storage device 300 including a plurality of spaced flanges 310 which extend from main body 12 into instrument housing 20. Preferably, flanges 310 are flexible, allowing for an instrument 22 to be pushed past flanges 310 into instrument housing 20, whereby the frictional force applied by flanges 310 to the instrument 22 aides in retaining the instrument 22 within housing 20. In a similar manner, flexible fingers 410 extending circumferentially about main body 12 of an alternative storage device 400 apply a frictional force to an instrument 22 to aid in retention of instrument 22 within housing 20 as depicted in FIGS. 10A and 10B. In yet another embodiment, a storage device 500 depicted in FIGS. 11a and 11b includes integral depressions 510 formed in main body 12, which are sized to interact with parts of an instrument 22 to aid in retention of instrument 22 within housing 20. In the preferred embodiment shown, depressions 510 are circular depressions formed within housing 20 that are sized to interact with an elbow 512 and end portion 513 of instrument 22. In this embodiment, storage device 500 is also shown with an optional sump 515 formed in bottom portion 36 including a top grate 516 depicted in FIG. 11B, having drainage holes 518 therein to allow fluids from housing 20 to drain into sump 515, thereby separating any medical instrument stored within housing 20 from the fluids. Additionally, grate 516 provides a surface upon which an instrument may optionally rest within housing 20. Alternatively, sump 515 may be in the form of posts or finger-like structures extending from the bottom and/or sides of tapered bottom portion 36 (not shown).

Figure 12:
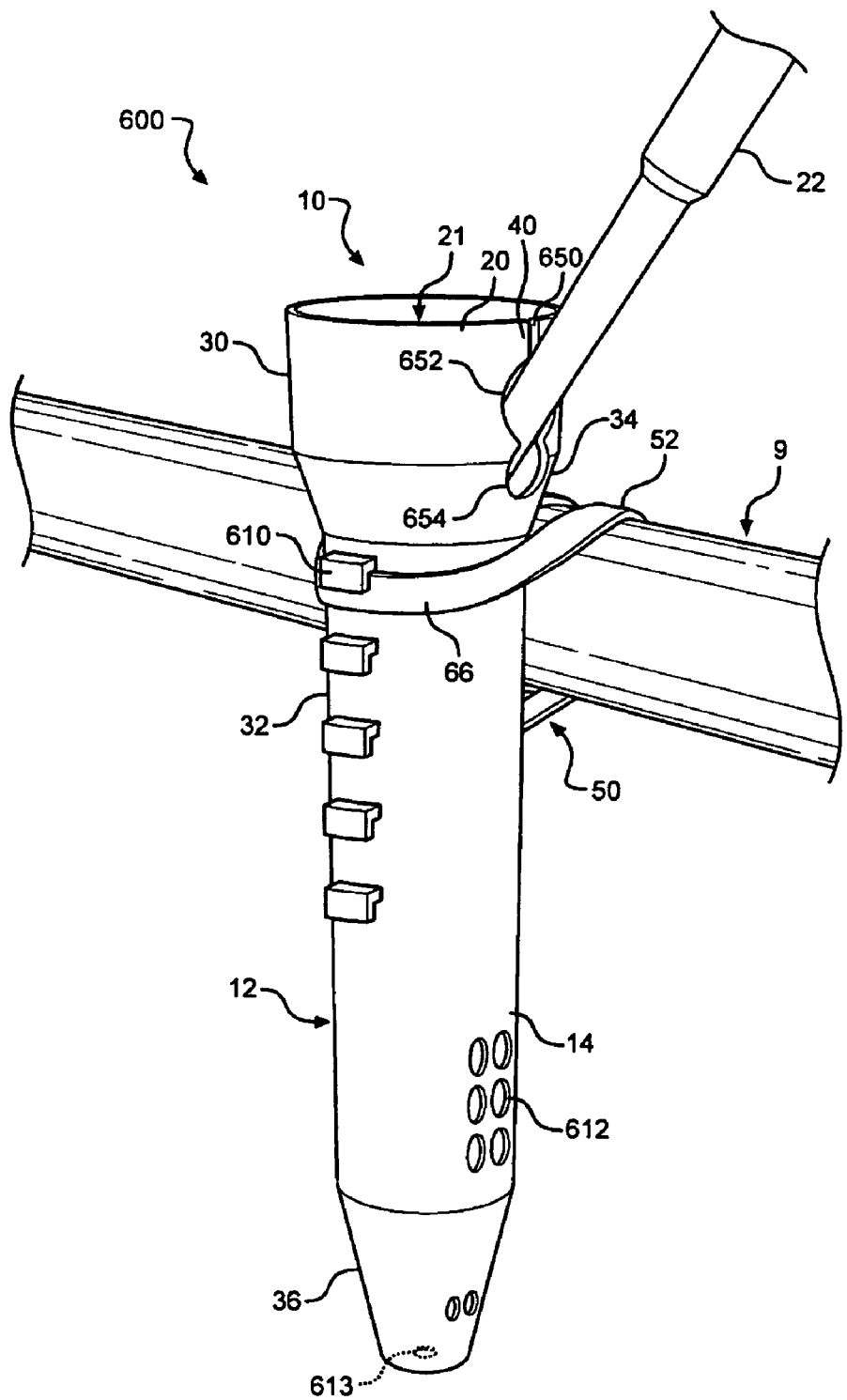
FIG. 12 is a perspective view of a medical instrument storage assembly of the present invention including an alternative storage device having external hooks.

FIG. 12 depicts another alternative storage device 600 including outer attachment means in the form of hooks 610 extending from main body 12. Storage device 600 is also depicted with optional air holes 612 extending through middle portion 32 to encourage airflow through instrument housing 20. Additionally, optional drain holes 613 are shown in bottom portion 36, which allows fluids to drain from housing 20. In the configuration shown, elastomeric loop 66 is connected to main body 12 through apertures 42 and 43 (not shown in FIG. 12). In use, storage device 600 is held against a support rail such as bed rail 9, and elastomeric loop 66 is stretched underneath bed rail 9, over bed rail 9, and looped over upper portion 30 and one of hooks 610. With this attachment method, elastomeric loop 66 provides a force to hold main body 12 against bed rail 9, while one of hooks 610 acts to retain elastomeric loop 66 in place with respect to main body 12. The use of hooks 610 eliminates the need for a fastener 60 for adjusting the size of elastomeric loop 66.

As should be readily understood from the attachment methods above, an applied force is necessary to hold a storage device of the present invention against a support surface. Elastomeric band member 52 is used to generate this force, as well as to create a frictional force to prevent slipping along and around the support surface. More specifically, the elastomeric properties of band member 52 are preferably established to create an optimal frictional force to prevent elastomeric band member 52 from sliding along a support rail. For example, elastomeric band member 52 can be designed to provide a secure attachment for semi-rigid, fully rigid or flexible storage device housings, depending on the materials utilized for storage device 10. Preferably, elastomeric band member 52 is latex-free. Optionally, the outer surface of a storage device of the present invention can be modified to enhance this frictional force. For example, a storage device may include concave or convex geometry that closely mimics the surface a bed rail, IV pole, head board or other equipment. Further, a storage device can include a modified outer surface finish, such as molded-in surface texture 78 depicted in FIG. 7.

The storage device of the present invention is preferably disposable such that each patient can have a dedicated storage device 10 and attachment mechanism 50. Advantageously, because the attachment mechanism 50 is integral to the storage device and inexpensive, the need for decontamination between uses of a stored instrument on the same, or different, patients is eliminated. Alternatively, the storage device may be comprised of appropriate materials that could be decontaminated and reused.

An important feature of the invention is the use of locking slot 40 to help secure a medical instrument in the storage device of the present invention, as depicted in FIG. 1. In accordance with a preferred use of the invention, a yankauer suction instrument 22 is retained within housing 20 in a convenient location along a support rail. The weight of suction tubing (not shown) attached to yankauer suction instrument 22 causes a moment force that tends to pull yankauer suction instrument 22 out of typical storage devices known in the art. Some commercial storage devices address this problem by the use of an external tubing clip, which adds cost and inconvenience. In contrast, the present invention utilizes integral locking slot 40 to temporarily lock yankauer suction instrument 22 in storage device 10 as demonstrated in FIG. 1. Reference will now be made to FIG. 12 in describing details of the first locking slot embodiment 40. Locking slot 40 preferably comprises a channel 650 formed in upper portion 30 that leads to a first substantially circular retention zone or aperture 652 and a second smaller substantially circular aperture 654, which together form a keyhole-type configuration. In a preferred embodiment, upper portion 30 is formed from semi-rigid plastic which allows it to flex and channel 650 to widen. In use, instrument 22 can be pushed down through channel 650 into one of slots 652 or 654 to be retained in locking slot 40.

Figure 15:
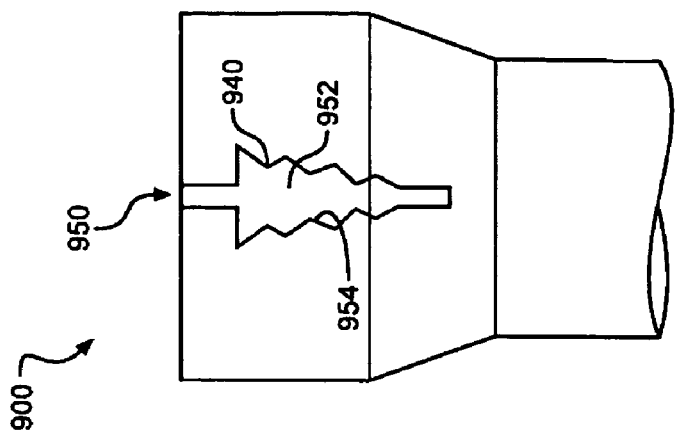
FIG. 15 is a partial side view of an alternative storage device including a third alternative locking slot configuration.
Figure 14:
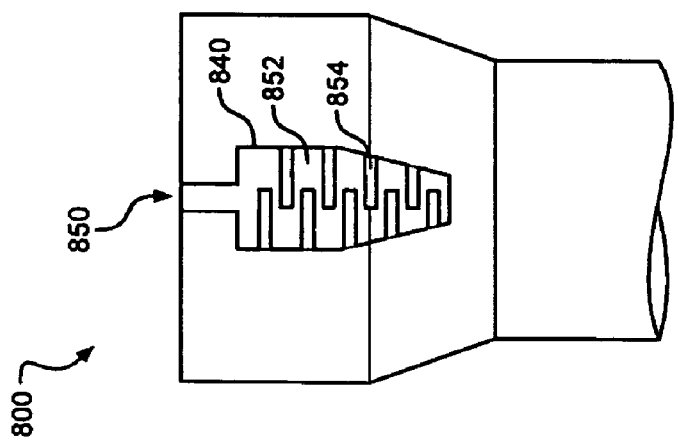
FIG. 14 is a partial side view of an alternative storage device including a second alternative locking slot configuration.
Figure 13:
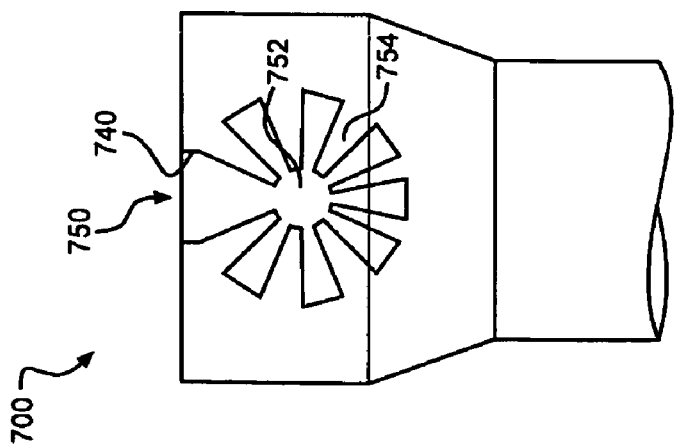
FIG. 13 is a partial side view of an alternative storage device including a first alternative locking slot configuration.

Alternative locking slot formations are depicted in FIGS. 13-15. More specifically, FIG. 13 depicts an alternative storage device 700 of the present invention including a locking slot 740 comprising a channel 750 which leads to a retention zone 752 defined by a plurality of flexible finger-like projections 754 which provide a frictional force to maintain a portion of an instrument within retention zone 752. FIG. 14 depicts an alternative storage device 800 including a locking slot 840 comprising a channel 850 which leads to a retention zone 852 including a plurality of opposing overlapping fingers 854 extending into retention zone 840. When portion of an instrument is pushed into retention zone 852 through channel 850, fingers 854 bend under the force of the instrument and allow a portion of the instrument to pass through at least some of fingers 854. In order for the portion of the instrument to pass back through channel 850, the instrument must pass back through at least some of fingers 854. Thus, fingers 854 provide a frictional force which aids in the retention of an instrument within retention zone 840. FIG. 15 depicts a final alternative storage device 900 including a locking slot 940 comprising a channel 950 which leads to a retention zone 952 defined in part by serrated edge portions 954 which aid in retaining a medical device within retention zone 952.

For each of the above-configurations, a user may retain at least part of a medical instrument within the respective locking slots by inserting a medical instrument into the housing such that at least a portion of the medical instrument extends through the locking slot. Preferably, housing 20 is flexible such that a user may press at least part of the medical instrument through the channel of the locking slot thereby flexing the housing and allowing at least part of the medical instrument to enter an aperture or retention zone of the locking slot through the upper slot, whereby the upper portion of the elongated housing flexes back to an original shape and aids in retaining the elongated medical instrument within the locking slot.

In the preferred embodiments shown, the storage device of the present invention allows free air circulation around a stored medical instrument. Air drying helps minimize the bio-burden on the medical instrument and storage device of the present invention, through desiccation of the microbes, thus aiding in infection control. Optionally, an ultraviolet (UV) light source (not shown) may be included in a storage device of the present invention to further help sanitize both the medical instrument and the storage device. Anti-microbial coatings on the walls of the storage device, or additives in the materials used to make the storage device may be utilized such that the housing includes an antimicrobial surface portions to deter microbial growth due to any fluids or contaminants that may accumulate on the walls of, or in the bottom of the storage device, thus providing additional reduction in bio-burden.

Although described with reference to preferred embodiments of the invention, it should be readily understood that various changes and/or modifications can be made to the invention without departing from the spirit thereof. For instance, while the preferred embodiment in FIG. 2 illustrates the use of a single elastomeric band member 52 threaded through first and second apertures 42 and 43 in storage device 10, it should be understood that elastomeric band member 52 could be fabricated with a variety of attachment means, such as a barb or mushroom, and that the storage device 10 itself could be modified to accommodate a range of elastomeric members and attachments. In addition, while the preferred embodiment depicts elastomeric band member 52 as having first and second ends 54 and 55 threaded through fastener 60, other shapes and geometries utilizing elastomeric materials, such as a continuous band or a die cut sheet, could be used to secure the storage device to bed rails, IV poles, head board rails and other equipment. Although a spring-biased fastener has been depicted herein, it should be understood that other types of fasteners such as clips or a fastener allowing one-way adjustment of the elastomeric band member 52, such as a truncated cone fastener or a metal member with a barbed hole, could be utilized. Further, while one preferred embodiment illustrates a storage device primarily designed to work with a yankauer suction instrument, a family of storage devices of varying sizes can be designed to accommodate different medical instruments, and each member of the family of devices may have a different method of temporarily securing the medical instrument in the holder between uses. In addition, the storage device of the present invention can be incorporated into the packaging of a medical device or instrument, thus allowing for a more economical way to package and store the device. Finally, the particular shape and construction of the housing could vary. For instance, the housing could have any uniform size/geometry, including circular, oval, polygonal or the like cross-sections. In any case, the invention is only intended to be limited by the scope of the following claims.

I claim:

1. A medical instrument holder assembly comprising:
   an elongated medical instrument;
   a support rail; and
   a medical storage device including:
      a main body including at least one side wall defining an elongated housing receiving said elongated medical instrument, wherein the main body comprises an upper portion, and said upper portion includes a locking slot formed therein adapted to receive at least a portion of the elongated medical instrument to selectively retain the elongated medical instrument within the housing; and
      a universal attachment mechanism including an elastomeric band member having a first end and a second end, and a fastener adapted to fit over the first and second ends of the elastomeric band member to selectively form an elastomeric loop; wherein the elastomeric loop is adapted to encircle the main body of the medical storage device and the support rail in order to selectively couple the medical storage device to the support rail.

2. The medical instrument holder assembly of claim 1, wherein the support rail is selected from the group consisting of a bed rail, an intravenous pole, a portion of a head board, a headwall, and a piece of equipment.

3. A medical storage device comprising:
   a main body including at least one side wall defining an elongated housing adapted to receive an elongated medical instrument, wherein said main body comprises an upper portion, and said upper portion includes a locking slot formed therein adapted to receive at least a portion of an elongated medical instrument to selectively retain the elongated medical instrument within the housing; and
   a universal attachment mechanism including an elastomeric band member having a first end and a second end, and a fastener adapted to fit over the first and second ends of the elastomeric band member to selectively form an elastomeric loop; wherein the elastomeric loop is adapted to encircle the main body of the medical storage device and the support rail in order to selectively couple the medical storage device to the support rail.

4. The medical storage device of claim 3, further comprising an attachment means on the main body for connecting the elastomeric band member to the main body.

5. A medical storage device comprising:
   a main body including at least one side wall defining an elongated housing adapted to receive an elongated medical instrument and a plurality of holes formed in the main body; and
   a universal attachment mechanism including an elastomeric band member having a first end and a second end, and a fastener adapted to fit over the first and second ends of the elastomeric band member to selectively form an elastomeric loop; wherein the elastomeric loop is adapted to encircle the main body of the medical storage device and the support rail in order to selectively couple the medical storage device to the support rail.

6. The medical storage device of claim 3, further comprising an internal retention mechanism adapted to aid in retaining a medical device within the housing.

7. The medical storage device of claim 3, further comprising an external retention feature formed on the main body and adapted to aid in retaining the medical device holder against a support rail.

8. The medical storage device of claim 3, wherein the main body further comprises a bottom portion including a sump formed in the bottom portion of the housing and adapted to prevent an instrument stored in the housing from contacting any fluid accumulated in the bottom portion of the housing.

9. The medical storage device of claim 3, further comprising at least one hook formed on the main body and adapted to aid in the retaining the elastomeric loop in place against the main body when the elastomeric loop encircles the main body.

10. A medical storage device comprising:
    a main body including at least one side wall defining an elongated housing adapted to receive an elongated medical instrument; and
    a universal attachment mechanism including an elastomeric band member having a first end and a second end, and a fastener adapted to fit over the first and second ends of the elastomeric band member to selectively form an elastomeric loop; wherein the elastomeric loop is adapted to encircle the main body of the medical storage device and the support rail in order to selectively couple the medical storage device to the support rail, wherein the fastener includes a housing having at least one aperture therein adapted to receive the first and second ends of the elastomeric band member, and wherein the fastener can be moved distally and proximally along the elastomeric band member to allow adjustment of the elastomeric loop.

11. The medical storage device of claim 3, wherein the housing is adapted to hold an elongated medical instrument selected from the group consisting of a trocar, scissors, a scalpel, a thermometer and a yankauer suction instrument.

12. A medical storage device comprising:
    a main body including at least one side wall defining an elongated housing adapted to receive an elongated medical instrument, wherein the housing includes an antimicrobial surface portion to deter microbial growth; and
    a universal attachment mechanism including an elastomeric band member having a first end and a second end, and a fastener adapted to fit over the first and second ends of the elastomeric band member to selectively form an elastomeric loop; wherein the elastomeric loop is adapted to encircle the main body of the medical storage device and the support rail in order to selectively couple the medical storage device to the support rail.

13. A method of safely storing a medical instrument comprising:
    securing a main body of a medical storage device to a support rail to retain the medical storage device against the support rail by extending an elastomeric band member from the main body of the medical storage device, establishing a loop about the support rail with the elastomeric band member and a fastener, and varying a size of the loop with the fastener; and inserting an elongated medical instrument into an elongated housing defined by said main body such that at least a portion of the elongated medical instrument extends through a locking slot formed in an upper portion of the main body and retains the elongated medical instrument within the housing.

14. The method of claim 13, further comprising:

inserting a first end of the elastomeric band through a first aperture formed in a middle portion of the main body;

inserting the first end of the elastomeric band through a second aperture formed in the middle portion of the main body adjacent the first aperture; and clamping the first end and a second end of the elastomeric band with the fastener to form the loop, such that the loop, when formed, is connected to the main body.

15. The method of claim 14, wherein securing the main body of the medical storage device to the support rail constitutes:

wrapping the first end of the elastomeric band around a first side of the support rail and wrapping the second end of the elastomeric band around an opposing side of the support rail before clamping the first and second ends of the elastomeric band with the fastener to form the loop, such that the loop is formed around the support rail; and adjusting the fastener to tighten the elastomeric loop about the support rail to retain the medical device holder against the support rail.

16. The method of claim 13, wherein securing the main body of the medical storage device to the support rail constitutes:

holding the main body against a support rail such that a middle portion of the main body is held against the support rail; and wrapping the loop from one side of the support rail to an opposing side of the support rail and looping the loop over at least one of upper and lower portions of the main body such that the loop is held against the middle portion of the main body and holds the medical storage device in place against the support rail.

17. The method of claim 16, wherein the support rail is substantially vertically aligned and the upper portion of the main body sits on an upper portion of the rail and aids in retaining the medical storage device in place against the rail.

18. The method of claim 13, wherein securing the main body of the medical storage device to the support rail constitutes:

adjusting the diameter of the loop using the fastener such that elastomeric loop is sized to wrap around the main body of the medical device holder and the support rail only with some amount of stretching of the loop;

holding the main body of the medical device holder in place against the support rail;

wrapping the loop around the main body and the support rail while holding the fastener in place against the main body until the fastener is adjacent an end of the loop; and looping the end of the elastomeric loop about the fastener to provide a loop and toggle connection to retain the medical device holder against the support rail.

19. The method of claim 13, wherein inserting an elongated medical instrument into an elongated housing defined by said main body such that at least a portion of the elongated medical instrument extends through a locking slot formed in an upper portion of the main body includes the steps of pressing at least part of the elongated medical instrument into an upper slot of the locking slot such that the upper portion of the elongated housing flexes and allows the at least part of the medical instrument to enter retention zone of the locking slot through the upper slot, whereby the upper portion of the elongated housing flexes back to an original shape and locks the elongated medical instrument within the locking slot.

20. The method of claim 13, further comprising: frictionally retaining the elongated medical instrument in the housing by engaging the elongated medical instrument with an internal retention mechanism provided in the housing.

21. The medical storage device of claim 10, further comprising an attachment means on the main body for connecting the elastomeric band member to the main body.

22. The medical storage device of claim 12, further comprising a plurality of holes formed in the main body.

* * * * *